(12) United States Patent
Zhang

(10) Patent No.: US 7,811,830 B2
(45) Date of Patent: Oct. 12, 2010

(54) PHOTOSENSITIZERS FOR PHOTODYNAMIC THERAPY AT INFRARED EXCITATION

(75) Inventor: Peng Zhang, Socorro, NM (US)

(73) Assignee: New Mexico Technical Research Foundation, Socorro, NM (US)

( * ) Notice: Subject to any disclaimer, the term of this patent is extended or adjusted under 35 U.S.C. 154(b) by 425 days.

(21) Appl. No.: 11/750,896

(22) Filed: May 18, 2007

(65) Prior Publication Data

US 2008/0286262 A1    Nov. 20, 2008

(51) Int. Cl.
*G01N 33/551* (2006.01)
(52) U.S. Cl. ............... 436/524; 436/525; 436/527; 436/172
(58) Field of Classification Search ............... None
See application file for complete search history.

(56) References Cited

U.S. PATENT DOCUMENTS 6,548,264 B1 * 4/2003 Tan et al. ............... 435/7.21
2003/0124564 A1 * 7/2003 Trau et al. ............... 435/6
2006/0223197 A1 * 10/2006 Vielsack ............... 436/524
2007/0254981 A1 * 11/2007 DiMaio et al. ............... 523/200

* cited by examiner

*Primary Examiner*—Christopher L Chin
(74) *Attorney, Agent, or Firm*—Robert W. Becker; Robert Becker & Associates

(57) ABSTRACT

A photosensitizer that is excitable via infrared radiation and is adapted to be used to treat a selected biological target. The photosensitizer comprises a core nanoparticle adapted to convert infrared radiation into a visible light emission, and a coating disposed about the core nanoparticle. The coating contains a light excitable agent that is adapted to be excited by the visible light emission from the core nanoparticle. The photosensitizer can be surface modified with an antibody to make the photosensitizer specific to the biological target that is to be treated. Such surface modified photosensitizer is introduced to the target site and irradiated with infrared radiation.

12 Claims, 1 Drawing Sheet

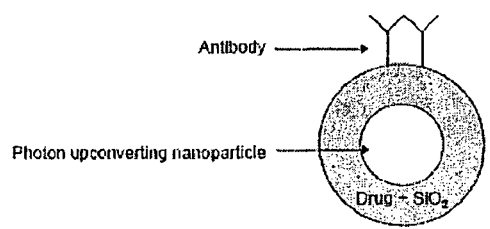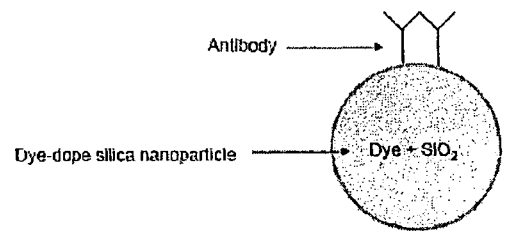
Figure 1.                                Figure 2.

PHOTOSENSITIZERS FOR PHOTODYNAMIC THERAPY AT INFRARED EXCITATION

BACKGROUND OF THE INVENTION

The present invention relates to photosensitizers excitable via infrared radiation, as well as to a method of producing such photosensitizers and the use of such photosensitizers to treat a selected biological target.

SUMMARY OF THE INVENTION

The present application provides a photosensitizer that is excitable via infrared radiation and comprises a core nanoparticle adapted to convert infrared radiation into a visible light emission, and a coating disposed about the core nanoparticle, wherein the coating contains a light excitable agent that is adapted to be excited by the visible light emission from the core nanoparticle.

The present application also provides a method of producing a photosensitizer that is excitable via infrared radiation, including the steps of providing a nanoparticle capable of converting infrared radiation into a visible light emission, and disposing a coating about the nanoparticle, wherein the coating contains a light excitable agent that is adapted to be excited by the visible light emission from the nanoparticle.

The present application also provides for the use of the photosensitizer to treat a selected biological target, including the steps of surface modifying the photosensitizer with an antibody to make the photosensitizer specific to the biological target that is to be treated, introducing the surface modified photosensitizer to the target site, and irradiating the surface modified photosensitizer with infrared radiation.

BRIEF DESCRIPTION OF THE DRAWINGS

The present application will now be described in conjunction with the accompanying schematic drawings, in which:

FIG. 1 shows one exemplary embodiment of a photosensitizer, and

FIG. 2 shows an exemplary application of the photosensitizer of FIG. 1.

DESCRIPTION OF SPECIFIC EMBODIMENTS

FIG. 1 shows an exemplary embodiment of a photosensitizer pursuant to the present invention, with the photosensitizer being indicated generally by the reference numeral 10.

In the illustrated embodiment, a photon upconverting core nanoparticle 11, which is capable of converting infrared radiation into a visible light emission, is surrounded by a coating 12. This coating is in the form of a silica ($SiO_2$) layer that contains a light excitable or activatable agent or drug, which is adapted to be excited by the visible light emission from the core nanoparticle, as will be discussed in detail subsequently. The coating 12 could also be a polymer coating.

The nanoparticles 11 are preferably of a size of up to 120 nm. The coating 12 is a thin coating of preferably less than 5 nm.

The following are two non-limiting examples for preparing a core nanoparticle 11.

Example 1

A solution or mixture of Yttrium (III) chloride ($YCl_3$, 0.2M), Ytterbium (III) chloride ($YbCl_3$, 0.2M), Erbium (III) chloride ($ErCL_3$, 0.2M) and diethylenetriaminepentaacetic acid (DTPA, 0.2M) is prepared in a volume ratio of $YCl_3$/$YbCl_3$/$ErCl_3$/DTPA=80/17/3/100. This solution is mixed with an aqueous sodium fluoride (NaF: 0.83M) solution in a volume ratio of 1/3, for example in a Teflon vessel. This vessel is then placed in a sealed metallic, for example stainless steel, container. The container is placed in an oven at about 120° C. for 3 hours.

After being allowed to cool, the resulting solution, including any solid precipitate, is transferred to, for example, a vial, which is then centrifuged. Thereafter, the supernatant is removed, and the remaining white solid is washed thoroughly with methanol ($CH_3OH$) by alternating sonication (for example in an ultrasonic bath) and centrifuging. The white solid is then dried in air or in an oven. The solid emits strong green light (~537 nm) and some red light (~650 nm) upon irradiation with an Infrared source (~975 nm).

Instead of the foregoing solution, a solution of Yttrium (III) chloride ($YCl_3$, 0.2M, Ytterbium (III) chloride ($YbCl_3$, 0.2M) and Thulium (III) chloride ($TmCl_3$, 0.2M) having the volume ratio of $YCl_3$/$YbCl_3$/$TmCl_3$/DTPA=82.7/17/0.3/100 can be used. In this case, the final product emits strong blue light (~477 nm) and some red light (~650 nm) upon irradiation with an infrared source (~975 nm).

Example 2

An aqueous solution of Yttrium (III) chloride ($YCl_3$, 0.2M), Ytterbium (III) chloride ($YbCl_3$, 0.2M) and Erbium (III) chloride ($ErCL_3$, 0.2M) in a volume ratio of $YCl_3$/$YbCl_3$/$ErCl_3$=80/17/3 is prepared. 0.66 ml of this solution is added to a vial containing 0.8 g of Cetyltrimethylammoniumbromide (CTAB), 2.31 ml of n-hexanol and 2 ml of an aqueous sodium fluoride (NaF, 0.415M) solution that had previously been stirred for 1.5 hours. The new solution is stirred for 24 hours.

Methanol ($CH_3OH$) is added to the vial, which is then shaken. The solution is centrifuged, and the supernatant is removed. The remaining white solid is thoroughly washed with methanol by alternate sonication and centrifuging. The white solid is dried overnight in an oven at about 90° C. The white sold is then annealed at about 400° C. for 5 hours and is subsequently cooled.

The ratio of aqueous solution/CTAB/n-hexanol (by weight) can be 50/15/35, 40/20/40 and 20/30/50. The ratio of $YCl_3$/$YbCl_3$/$ErCl_3$ (by volume) can be 80/18/2, 80/17/3 and 80/17/4. The above example shows the case of aqueous solution/CTAB/n-hexanol (by weight)=50/15/35 and $YCl_3$/$YbCl_3$/$ErCl_3$ (by volume)=80/17/3.

One example for coating photon upconverting nanoparticles with a silica layer that contains a light excitable agent follows.

Example 3

30 mg of photon upconverting nanoparticles are placed in a glass vial, to which are added 80 ml of n-propanol. The substituents are sonicated for at least 30 minutes, 8.94 ml of 28% ammonia, 7.5 ml of aqueous solution of selected light excitable agents, such as 1 mM Merocyanine 540 as an aqueous solution, and 0.008 ml tetraethyl orthosilicate (TEOS) are added to the vial accompanied by vigorous stirring. Stirring is continued for 12 hours. The resulting solution is centrifuged, and the supernatant is removed.

The remaining solid is thoroughly washed with methanol by alternate sonication and centrifuging. After final washing, a small amount of deionized water is added to keep the thus thinly-coated nanoparticdes in a slurry form.

FIG. 2 shows an exemplary application of the photosensitizer pursuant to the present application, namely for photodynamic therapy at infrared excitation.

The coating 12 has been surface treated with an antibody to make the photosensitzer specific to a biological target, such as the target 14, that is to be treated. One example of an antibody, in this case to target MCF-7/AZ breast cancer cells, is the mouse monoclonal antibody, anti-MUC1/episialin.

After introduction or implantation at a target site, the surface modified photosensitizer is irradiated with infrared radiation, for example from an IR laser. The nanoparticle 11 converts the infrared radiation into a visible light emission, as shown. Upon irradiation of the agent contained in the coating 12 by the visible light, the agent reacts with oxygen, leading to the formation of reactive oxygen species (ROS), which are very active and will damage and/or kill the targeted biological cells.

An example for surface modifying the coating 12 of the photosensitizer with an antibody to make the photosensitizer specific to a biological target that is to be treated follows Example 4

0.1 grams of previously prepared coated nanoparticles are washed twice in 10 ml of a wash/coupling buffer comprised of a phosphate buffer solution (PBS) having a pH of 8.9. The nanoparticies are resuspended in 9.5 ml of an activation buffer comprised of 2M sodium carbonate solution by sonication or vortexing. 1 g of CNBr is dissolved in 0.5 ml acetonitrile, and the solution is added dropwise to the nanoparticle suspension accompanied by stirring. The reaction is allowed to continue for 5 minutes. The nanoparticles are then washed in a large volume of cold deionized water, and are then washed with cold wash/coupling buffer. The nanoparticles are resuspended in 5 ml of cold wash/coupling buffer. The antibody that is to be coupled to the coating of the nanoparticies is dissolved in 5 ml of the wash/coupling buffer at a concentration corresponding to 1 to 10 times in excess of the calculated monolayer. The nanoparticle suspension and the antibody solution are combined, and the suspension is maintained for 24 hours with constant mixing. This is followed by washing and resuspension of the resulting nanoparticles in a storage buffer comprised of a phosphate buffer solution having a pH of 7-7.5. The thus surface modified photosensitizer can be stored in a cold climate until ready for use.

In an invitrotest, 0.5 ml of cell suspension, i.e. a target site, was placed in a covered Petri dish having a glass bottom for viewing. 0.1 ml of antibody-modified photosensitizers in a PBS buffer solution, and 1 μl of dye solution (1 mg/ml) used for labeling dead/dying cells were added to the cell suspension, thoroughly mixed, and incubated for 15 minutes at room temperature. An infrared light source of 975 nm was directed at the target cells/surface-modified photosensitizers to provide irradiation for a certain period of time.

For an in vivo application, an appropriate amount of antibody-modified photosensitizer solution would be introduced to target tissue or tissues by, for example, subcutaneous or intramuscular injection. An infrared light source of, for example, 975 nm would then be directed to the targeted tissues and/or cells, with irradiation taking place for a specific period of time.

The present invention is, of course, in no way restricted to the specific disclosure of the specification and drawings, but also encompasses any modifications within the scope of the appended claims.

What I claim is:

1. A photosensitizer that is excitable via infrared radiation, comprising:
   a core nanoparticle that is capable of converting infrared radiation into a visible light emission; and
   a coating disposed about said core nanoparticle, wherein said coating contains a light excitable agent that is capable of being excited by the visible light emission from said core nanoparticle.

2. A photosensitizer according to claim 1, wherein said coating is silica or a polymer.

3. A photosensitizer according to claim 1, wherein said coating is surface modified by an antibody to make the photosensitizer specific to a biological target that is to be treated.

4. A photosensitizer according to claim 1, wherein said core nanoparticle is a photon upconverting core nanoparticle.

5. A photosensitizer according to claim 1, wherein said core nanoparticle is made from a starting solution containing at least Yttrium (III) chloride and Ytterbium (III) chloride.

6. A method of producing a photosensitizer that is excitable via infrared radiation, including the steps of:
   providing a nanoparticle that is capable of converting infrared radiation into a visible light emission; and
   disposing a coating about said nanoparticle, wherein said coating contains a light excitable agent that is capable of being excited by the visible light emission from said nanoparticle.

7. The method of claim 6, wherein said coating step comprises mixing together the nanoparticle, a coating material, and the agent in a sol-gel reaction.

8. The method of claim 6, including the further step of surface modifying said photosensitizer with an antibody to make the photosensitizer specific to a biological target that is to be treated.

9. The method of claim 8, wherein said step of surface modifying comprises attaching antibody molecules covalently to a surface of said coating.

10. The method of claim 6, wherein said coating step comprises disposing silica or a polymer about said nanoparticle.

11. A method according to claim 6, wherein said step of providing a nanoparticle comprises providing a photon upconverting core nanoparticle.

12. A method according to claim 6, wherein said step of providing a nanoparticle comprises providing a nanoparticle made from a starting solution containing at least Yttrium (III) chloride and Ytterbium (III) chloride.

* * * * *